United States Patent [19]

Masuhara et al.

[11] Patent Number: 5,308,886
[45] Date of Patent: May 3, 1994

[54] PHOTOSETTING RESIN FOR MAKING STRONG, TOUGH RESIN ARTICLES

[75] Inventors: Eiichi Masuhara, Tokyo; Shigeo Komiya, Urawa; Takeyuki Sawamoto, Tokyo, all of Japan

[73] Assignee: Japan Institute of Advanced Dentistry, Tokyo, Japan

[21] Appl. No.: 820,625

[22] PCT Filed: Apr. 19, 1991

[86] PCT No.: PCT/JP91/00451

§ 371 Date: Jan. 28, 1992

§ 102(e) Date: Jan. 28, 1992

[87] PCT Pub. No.: WO91/16364

PCT Pub. Date: Oct. 31, 1991

[30] Foreign Application Priority Data

Apr. 20, 1990 [JP] Japan ................................. 2-104677

[51] Int. Cl.$^5$ ........................ C08F 2/48; C08F 220/26; C08K 3/22
[52] U.S. Cl. ............................................ 522/81; 522/181; 522/183; 523/116; 523/118; 526/320; 526/323.1; 526/323.2
[58] Field of Search ........................ 522/81, 181, 183; 526/320, 323.1, 323.2; 523/116, 118

[56] References Cited

U.S. PATENT DOCUMENTS

| | | | |
|---|---|---|---|
| 4,388,421 | 6/1983 | Suzuki et al. | 523/118 |
| 4,394,494 | 7/1983 | Miyake et al. | 523/105 |
| 4,910,275 | 3/1990 | Yamazaki et al. | 526/425 |

FOREIGN PATENT DOCUMENTS

| | | |
|---|---|---|
| 55-102618 | 8/1980 | Japan . |
| 58-179212 | 8/1983 | Japan . |
| 62-180782 | 8/1987 | Japan . |
| 63-162710 | 7/1988 | Japan . |
| 64-51413 | 2/1989 | Japan . |
| 64-60614 | 3/1989 | Japan . |
| 64-87608 | 3/1989 | Japan . |

*Primary Examiner*—Susan Berman
*Attorney, Agent, or Firm*—Nixon & Vanderhye

[57] ABSTRACT

A photosetting resin comprising a liquid monomer composition and a photopolymerization initiator, the monomer composition containing a compound represented by the following formula (1) and a compound represented by the following formula (2) in a weight ratio within the range from 97:3 to 50:50:

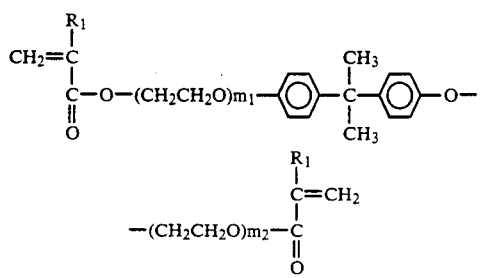

(wherein $R_1$ is H or $CH_3$, and $0 \leq m_1 + m_2 \leq 4$)

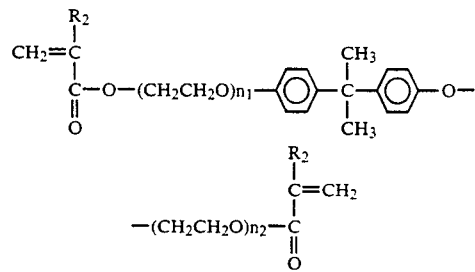

(wherein $R_2$ is H or $CH_3$, and $5 \leq n_1 + n_2 \leq 12$).

This photosetting resin can provide a cured resin which is excellent in both strength and toughness.

3 Claims, No Drawings

PHOTOSETTING RESIN FOR MAKING STRONG, TOUGH RESIN ARTICLES

TECHNICAL FIELD

The present invention relates to a resin which is cured by photopolymerization. More particularly, the invention pertains to a photosetting resin which, when used as producing material for resin molded products, can provide a set or cured material which is excellent in strength as well as in toughness.

BACKGROUND ART

Hitherto, as photosetting resins, there have been used monomer compositions added with a small quantity of a photopolymerization initiator, said monomer compositions comprising a polyfunctional monomer such as 1,6-hexanediol di(meth)acrylate, triethylene glycol di(meth)acrylate, dicyclopentanyl di(meth)acrylate, tri((meth)acryloxymethyl) isocyanurate, urethane-modified di(meth)acrylate, epoxy-modified di(meth)acrylate, trimethylolpropane tri(meth)acrylate and the like, and further, if necessary, with a monofunctional monomer such as methyl (meth)acrylate, ethyl (meth)acrylate, dicyclopentanyl (meth)acrylate, hydroxyethyl (meth)acrylate, N-vinylpyrrolidone and the like.

There are also used colored photosetting resins prepared by adding a dye or pigment to said photosetting resins and ones added with an organic or inorganic filler to regulate the color tone or mechanical properties of the set or cured resins.

These photosetting resins can be set by irradiation of light such as ultraviolet light for a short time, from several seconds to several minutes, to give a desired set or cured resin. Further, most of these photo-setting resins are one-pack type and very easy to handle. They also have a characteristic that the thickness where setting takes place is usually within a range from several μm to several hundred μm, so that they find a wide scope of application including, for instance, coating material, printing ink and adhesive.

Recently, there has been developed a photosetting resin as a material for dental use, which can be set with visible light. In the case of this photosetting resin for dental use, since visible light is used for setting the resin, there can be relatively easily obtained a set or cured resin even when the photosetting resin has a large thickness of up to 5-6 mm or is an opaque one mixed with a filler. Accordingly, this type of photosetting resin is applied advantageously as a filling resin for cavities or hard resin to be used as resin veneer for cast crown, and for other dental applications.

A need is arising for further expanding the scope of application of the photosetting resins by making the most of their advantages such as mentioned above. Japanese Patent Application Laying Open (KOKAI) No.58-179212, for instance, discloses a photosetting resin applied as a material for producing resin molded products.

However, in application of these conventional photosetting resins to formation of the resin molded products, the obtained molded products were indeed excellent in surface hardness and other properties such as tensile and compressive strength, but generally the molded products would become hard and fragile so that only a slight flaw to the molded product could result in break thereof.

For instance, in case a photosetting resin having said dicyclopentanyl diacrylate as a monomer component is applied to a hard coating material, there can be obtained a coating film having excellent surface hardness. But in case said photo-setting resin is made into a plate-shaped molded article having a thickness of about 2-3 mm by using a frame, there is merely obtained a frangible molded article which is easily broken when given only a slight deformation.

Such defects of the conventional photosetting resins are due to the very small breaking strain of the set or cured resins as noticed in a bending test or tensile test of said resins.

Such problem of fragility of the conventional photosetting resins can be overcome by enlarging the breaking strain of the set or cured ones.

But if a monomer having soft properties is simply used as a constituent of a photosetting resin in a bid for attaining said object, although the breaking strain will be enlarged, there will also arise another problem: sharp reduction of mechanical strength of the set resin, making it impossible to obtain a molded article having well satisfactory mechanical properties.

Thus, the conventional photosetting resins were frangible and poor in toughness and therefore unsuited for use as a material for forming strong and tough resin molded articles.

DISCLOSURE OF THE INVENTION

The present inventors have made assiduous studies for solving said prior art problems and, as a result, succeeded in obtaining a tough photosetting resin by adding a photopolymerization initiator to a liquid monomer composition comprising, in a ratio by weight of from 97:3 to 50:50, a compound represented by the following formula (1) and a compound represented by the following formula (2):

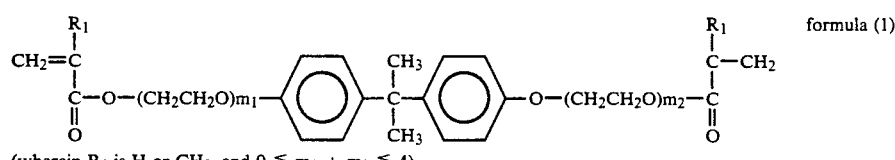

(wherein $R_1$ is H or $CH_3$, and $0 \leq m_1 + m_2 \leq 4$)

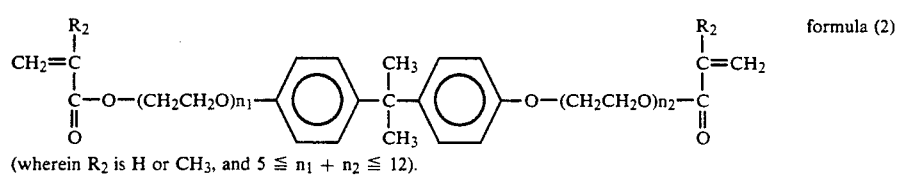

(wherein $R_2$ is H or $CH_3$, and $5 \leq n_1 + n_2 \leq 12$).

The liquid monomer composition used in the present invention is characterized by that, regarding the monomer components constituting the photosetting resin, bisphenol A di(meth)acrylate having an ethylene oxide additive molar number of 4 or less is used as the first component and bisphenol A di(meth)acrylate having an ethylene oxide additive molar number in a range from of 5 to 12 is used as the second component.

The present invention will be described in further detail hereinbelow.

Bisphenol A di(meth)acrylate having the ethylene oxide additive molar number of 4 or less, which is used as the first component of the monomer components constituting the photosetting resin of this invention, is a component which serves for affording strength such as tensile and bending strength to the set resin. Bisphenol A di(meth)acrylate having the ethylene oxide additive molar number in the range of from 5 to 12, used as the second component of the monomer components, is a component which increases breaking strain of the set resin material.

In the present invention, it is critical that the weight ratio of said two monomer components is within the range from 97:3 to 50:50, preferably from 95:5 to 70:30. If the ratio of the first component is higher than the above-defined range, although strength of the set material will be high, breaking strain will be lessened to make the molded product frangible. Also, if the ratio of the second component exceeds the above-defined range, although breaking strain will be increased, the strength will be excessively lowered and a molded product having a desired strength can not be obtained.

Thus, the feature of the present invention resides in that said two monomer components are used in a weight ratio within the range specified in the present invention so as to increase both of strength and breaking strain.

Therefore, if the ethylene oxide additive molar number of the two monomer components according to this invention is outside the range defined in this invention, the set product of the photosetting resin will be reduced in strength and/or its breaking strain will be lessened, disadvantageously resulting in unsatisfactory toughness of the set resin.

Regarding the monomer of the first component used in the present invention, which is selected from bisphenol A di(meth)acrylates having the ethylene oxide additive molar number of 4 or less, it is possible to use in combination, for example, said di(meth)acrylate with said molar number of 0 and the one with said molar number of 4. The same is true of the second component.

As the photopolymerization initiators usable in the present invention, there can be mentioned ordinary photopolymerization initiators for photopolymerization by ultraviolet ray such as benzoin ethers, benzophenones, thioxanthones, acetophenones, 1-hydroxycyclohexyl phenyl ketone and the like. It is also possible to use photopolymerization initiators having sensitivity in a visible light region, such as benzyl, camphorquinone, camphorquinone derivatives, thiopyrylium salts and the like.

It is desirable that the photopolymerization initiator be used usually in an amount within a range of from 0.01 to 10% based on the weight of the monomer components, but it is especially desirable that said range is from 0.05 to 1% in case of producing a molded article having a relatively large thickness.

Further, in the present invention, a tertiary amine or an organic peroxide may be added as reaction assistant, in addition to the photopolymerization initiator, for the purpose of further enhancing a setting or curing rate. Also, a thermal polymerization inhibitor such as hydroquinone, hydroquinone monometyl ether and the like may be added for the purpose of improving storage stability of the photosetting resin.

Still further, in the present invention, a monofunctional (meth)acrylate may be added in a weight ratio within a range of from 90:10 to 40:60, preferably from 80:20 to 60:40 based on the monomer components consisting of said first and second components, for the purpose of further improving the properties of the photosetting resin.

As examples of said third component, there can be cited methyl (meth)acrylate, ethyl (meth)acrylate, propyl (meth)acrylate, butyl (meth)acrylate, hexyl (meth)acrylate, cyclohexyl (meth)acrylate, benzyl (meth)acrylate, (meth)acrylic acid, hydroxyethyl (meth)acrylate and the like.

Especially, if methyl methacrylate or ethyl methacrylate is used as the third component, it will be possible to further enhance toughness of the photosetting resin of this invention.

In the present invention, an organic or inorganic filler and/or a colorant such as a dye or pigment may be added according to the purpose of use of the product in the same way as used in the conventional photosetting resins.

As the inorganic fillers usable in the present invention, there can be mentioned silicon dioxide, titanium dioxide, glass powder and the like, which are ordinarily used.

Especially in case the photosetting resin of this invention is applied as a dental material having a color resembling that of the teeth, it is preferred to use a filler with a high refractive index such as titanium dioxide, zirconium dioxide, alumina and the like in a very small amount for maximizing the toughness characteristic of the resin which is the feature of the present invention. Use of the filler with a high refractive index such as mentioned above, even though in a small amount, enables obtainment of an opalescent or translucent resin, namely a resin with a color closely analogous to that of the teeth. Also, the resin is not made frangible by use of said filler since the amount of said filler added is so small that toughness possessed by the photosetting resin of this invention is not impaired.

The added amount of the filler with a high refractive index such as titanium dioxide, zirconium dioxide, alumina and the like is preferably defined to a range of from 0.001 to 1% by weight, more preferably from 0.01 to 0.1% by weight.

It is also desirable that an average particle size of said filler with a high refractive index is usually in a range of from 0.02 to 1 μm, preferably from 0.05 to 0.5 μm. By defining the average particle size of the filler within said range, it will be possible to obtain a resin having a desired color tone although the amount of the filler added is small, and also toughness of the resin won't be impaired.

Thus, by adding the filler with a high refractive index such as mentioned above to the photosetting resin of this invention while regulating the amount and average particle size of the filler within the abovedefined ranges, it is possible to make a resin having high toughness, which is the feature of this invention, as well as an aesthetic quality akin to the color tone of the teeth.

A method for setting or curing the photosetting resin of this invention will be described below.

For setting or curing the photosetting resin of this invention, there can be used a commonly-employed type of ultraviolet light source such as a high pressure mercury lamp and ultra-high pressure mercury lamp, but in case of setting a molded product having a large thickness, it is recommended to prepare a photosetting resin by using a photopolymerization initiator having sensitivity to visible light and to employ a light source which generates visible light such as a xenon or halogen lamp.

Irradiance of the light applied is preferably adjusted to be in a range of from 1 to 50 mW/cm$^2$, more preferably from 10 to 30 mW/cm$^2$. Irradiation time is usually set between one second and about 30 minutes, practically being preferably in a range of from about 30 seconds to about 20 minutes.

For preparing a resin molded article by using the photosetting resin of this invention, a method is employed in which the photosetting resin is filled in an ordinary molding frame, then light is applied to the resin to cure it. After curing has been completed, the cured product is taken out of the frame.

The frame used here should be the one which allows irradiation without the light being intercepted by the molded product to be cured. Such a frame may be, for instance, the one which is at least partly made of such material as glass, poly-4-methyl-1-pentene, transparent polypropylene or the like.

BEST MODE FOR CARRYING OUT THE INVENTION

The present invention will be described more particularly below with reference to the examples thereof.

EXAMPLES

Example 1

66 parts by weight of 2,2'-bis(4-methacryloxyethoxyphenyl)propane and 34 parts by weight of 2,2'-bis(4-methacryloxypentaethoxyphenyl)propane were weighed into a brown glass bottle, followed by addition of 0.5 part by weight of d,l-camphorquinone and 0.75 part by weight of dibenzoyl peroxide as a polymerization initiator, and the mixture was stirred well to give a photosetting resin of this invention.

Then this liquid resin was filled in a polypropylene-made tube, 4.6 mm in inner diameter and 70 mm long, in such a way that no air cells would get thereinto, and the packed tube, after sealed, was irradiated with visible light by using a commercially available visible light irradiator (α-Light mfd. by Morita Tokyo Seisakusho, Ltd.) for 20 minutes to effect polymerization of the resin.

After completion of irradiation with the visible light, the cured resin composition was taken out of the tube. The resin thus obtained was hard and transparent.

Both ends of the resulting resin were then cut out to prepare a 40 mm long rod-like test piece and it was subjected to a three-point bending test by using an Instron universal tester. The bending test was conducted under the following conditions: span length=20 mm, crosshead speed=0.5 mm/min.

Values for the flexural breaking strain energy per volume were calculated by dividing the value for the flexural breaking strain energy by the volume of the test piece ($\pi$ (2.3 mm)$^2 \times$ 20 mm = 332 mm$^3$).

The test showed that the resin of the instant example had a bending strength of 16.5 kg f/mm$^2$ and a flexural breaking strain of 13%, which indicate excellent strength of the resin. The test also showed a flexural breaking strain energy of 48 kg f·mm, indicating high toughness of the resin.

The flexural breaking strain energy was determined as an area of the section where the stress-strain curve obtained in the bending test encompassed the strain axis.

Examples 2, 3 and 4

The photosetting resin samples of this invention were prepared in the same way as Example 1 by using the monomer compositions indicated by 2, 3 and 4 in Table 1, and the prepared photosetting resin samples were subjected to photopolymerization by visible light irradiation.

The results of the bending test conducted on the resins thus obtained are also shown in Table 1.

The resulting resins of Examples 2, 3 and 4 all had a high bending strength and also showed a large flexural breaking strain energy and excellent toughness.

Comparative Examples 1 and 2

Homopolymers of 2,2'-bis(4-methacryloxyethoxyphenyl)propane and 2,2'-bis(4-methacryloxypentaethoxyphenyl)propane were prepared by the same operations as in Example 1, and they were subjected to the bending test.

The homopolymer of 2,2'-bis(4-methacryloxyethoxyphenyl)propane was high in bending strength but its bending strain was as small as 9%, indicating its hard and frangible characteristic (see R1 in Table 1), while the homopolymer of 2,2'-bis(4-methacryloxypentaethoxyphenyl)propane showed a notably large bending strain of 54% but its bending strength was as low as 1.9 kg f/mm$^2$.

Also, the flexural breaking strain energy of these homopolymers was less than half that of the resins obtained in Examples 1–4, indicating poor toughness of said homopolymers.

Comparative Example 3

A resin composition was prepared by following the same procedure as Example 1 while adopting the compositional ratio of the monomers outside the range specified in the present invention as shown under R3 in Table 1.

The resin obtained in this example was transparent but rather soft. The bending test of this resin showed its low bending strength: 13.2 kg f/mm$^2$. The flexural breaking strain energy of this resin was also low: 36 kg f·mm.

Comparative Example 4

A resin composition was prepared according to the same procedure as Example 1 except for the use of 2,2'-bis(4-acryloxydiethoxycyclohexyl)propane as a monomer.

The obtained resin was very soft and showed a large flexural breaking strain of 17%, which was comparable with those of the resins of Examples 2 and 3, but its bending strength was intolerably low: 5.0 kg f/mm$^2$.

Also, the flexural breaking strain energy as determined from the stress-strain curve was as low as 18 kg f·mm, indicating poor toughness of this resin.

Example 5

By the same operations as in Example 1, there was prepared a photosetting resin of this invention by adding 0.6 part by weight of d,l-camphorquinone and 0.6 part by weight of N,N-dimethylparatoluidine as a polymerization initiator to a monomer composition consisting of 62 parts by weight of 2,2'-bis(4-methacryloxyethoxyphenyl)propane, 18 parts by weight of 2,2'-bis(4-methacryloxypentaethoxyphenyl)propane and 20 parts by weight of methyl methacrylate, and the prepared resin composition was photopolymerized with visible light irradiation in the same way as in Example 1.

The resin thus obtained was hard and transparent as those of Examples 1–4. The bending test of this resin showed that it had a bending strength of 19.3 kg f/mm$^2$ and a flexural breaking strain of 16%, indicating excellent strength of this resin.

Further, when the flexural breaking strain energy was determined in the same way as in Example 1, it was as large as 74 kg f·mm, indicating excellent toughness of this resin.

Examples 6–10

Base solutions for photosetting resin compositions of this invention were prepared with the monomer compositions shown in Table 2 in the same way as in Example 5, and the prepared base solutions were subjected to photopolymerization with visible light irradiation in the same way as in Example 5 to obtain the resins.

The results of the bending tests conducted on the thus obtained resins are also shown in Table 2. Any of these resins showed an excellent bending strength and a proper degree of flexural breaking strain. These resins also showed very large flexural breaking strain energy and excellent toughness.

Comparative Example 5

A base solution for resin composition was prepared in the same way as in Example 5 by adding a polymerization initiator to a monomer composition consisting of 80 parts by weight of 2,2'-bis(4-methacryloxyethoxyphenyl)propane and 20 parts by weight of methyl methacrylate.

This base monomer solution was photopolymerized in the same way as in Example 1 to prepare a resin. The resin was subjected to the bending test, which showed a satisfactorily high bending strength of 18.0 kg f/mm$^2$, but the flexural breaking strain was as low as 10%, indicating the hard and frangible characteristic of this resin. Also, the flexural breaking strain energy determined in the same way as described above was 40 kg f·mm, which was far smaller than those obtained in Examples 5–10, indicating poor toughness of this resin.

Example 11

In this example is discussed a preparation of a resin for dental use by adding an inorganic filler to a photosetting resin according to this invention.

A monomer composition consisting of 55 parts by weight of 2,2'-bis(4-methacryloxyethoxyphenyl)propane, 15 parts by weight of 2,2'-bis(4-methacryloxypentaethoxyphenyl)propane and 30 parts by weight of methyl methacrylate was mixed with 0.6 part by weight of d,l-camphorquinone and 0.75 part by weight of dibenzoyl peroxide and then further added with 0.02 part by weight of titanium dioxide having an average particle size of 0.26 μm as inorganic filler, and the mixture was stirred well to prepare a photosetting resin for dental use.

The photosetting resin thus prepared was polymerized by using visible light in the same way as in Example 1. The cured resin, being translucent and opalescent, had a close resemblance to tooth enamel and an admirable aesthetic quality.

For the purpose of evaluating aesthetic quality of the cured resin, the photosetting resin prepared in this Example was filled between two pieces of slide glass, each being made of blue plate glass, with a 0.5 mm thick Teflon spacer interposed therebetween, and cured in the same way as in Example 1. Light transmittance of the cured resin at a wavelength of 550 nm was measured by using a spectrophotometer. The result showed that the resin of this Example had a light transmittance of 71%.

The thus obtained resin was also subjected to the bending test of Example 1, which showed a bending strength of 19.3 kg f/mm$^2$, a flexural breaking strain of 18% and a flexural breaking strain energy of 92 kg f·mm, which indicated that the resin was excellent in both strength and toughness.

Example 12

A photosetting resin was prepared by following the same procedure as Example 11 except the amount of the inorganic filler added. The properties of the cured resin are shown in Table 3.

The cured resin of this Example was lower in transparency than the product of Example 11 and had a color tone resembling that of dentine and an excellent aesthetic quality. Light transmittance of this resin determined in the same way as in Example 11 was 49%.

The cured resin of this Example also had excellent toughness as noted from the results of the bending test shown in Table 3.

Comparative Example 6

In this comparative example is discussed a preparation of a photosetting resin having an aesthetic quality equal to that of the product of Example 11 by using the conventional techniques.

To a monomer composition consisting of 70 parts by weight of 2,2'-(4-methacryloxyethoxyphenyl)propane and 30 parts by weight of methyl methacrylate, there was added the same photopolymerization initiator as used in Example 11, followed by further addition of 9 parts by weight of silicon dioxide with an average particle size of 0.02 μm which is widely used for ordinary dental resins as an inorganic filler, thereby preparing a photosetting resin.

Curing of the photosetting resin thus prepared in the same way as in Example 11 gave a cured resin having an aesthetic quality almost equal to that of the product of Example 11. Light transmittance of this cured resin determined in the same way as in Example 11 was 72%.

However, the bending test of this cured resin showed that although its bending strength was 18.2 kg f/mm$^2$, the flexural breaking strain was as small as 8% and also the flexural breaking strain energy was as low as 19 kg f·mm. Thus, the cured resin of this comparative example was far lower in toughness than the product of Example 11.

Comparative Example 7

For the purpose of preparing a resin having an aesthetic quality equal to that of the product of Example 12, there was prepared a photosetting resin by following the same procedure as Example 12 except for addition of 20 parts by weight of silicon dioxide having an average particle size of 0.02 μm used in Comparative Example 6 as an inorganic filler. The results are shown in Table 3.

The cured version of the photosetting resin thus prepared had light transmittance of 52% and an aesthetic quality equal to that of the product of Comparative Example 6.

However, the bending test of the cured resin thus obtained showed that the bending strength, flexural breaking strain and flexural breaking strain energy of this resin were all far less than those of the product of Example 12, and thus said cured resin was weak and frangible.

TABLE 1

| Composition (wt %) | Bending strength (kgf/mm$^2$) | Flexural breaking strain (%) | Flexural breaking strain energy (kgf·mm) | Flexural breaking strain energy per volume (kgf·mm/mm$^3$) |
|---|---|---|---|---|
| 1 BPM1/BPM5 (66/34) | 16.5 | 13 | 48 | 0.14 |
| 2 BPM2/BPM5 (80/20) | 18.0 | 16 | 60 | 0.18 |
| 3 BPM1/BPM2/BPM3 (43/42/15) | 17.0 | 16 | 64 | 0.19 |
| 4 BPM1/BPA6 (90/10) | 18.5 | 14 | 58 | 0.17 |
| R1 BPM1 (100) | 18.4 | 9 | 21 | 0.06 |
| R2 BPM5 (100) | 1.9 | 54 | 17 | 0.05 |
| R3 BPM1/BPM5 (40/60) | 13.2 | 16 | 36 | 0.11 |
| R4 CHM (100) | 5.0 | 17 | 18 | 0.05 |

TABLE 2

| Composition (wt %) | Bending strength (kgf/mm$^2$) | Flexural breaking strain (%) | Flexural breaking strain energy (kgf·mm) | Flexural breaking strain energy per volume (kgf·mm/mm$^3$) |
|---|---|---|---|---|
| 5 BPM1/BPM5/MMA (62/18/20) | 19.3 | 16 | 74 | 0.22 |
| 6 BPM1/BPM5/MMA (47/23/30) | 18.8 | 17 | 89 | 0.27 |
| 7 BPM1/BPM4/MMA (40/15/45) | 19.0 | 14 | 62 | 0.19 |
| 8 BPM2/BPM5/MMA/EMA (54/16/25/5) | 18.8 | 18 | 84 | 0.25 |
| 9 BPM1/BPA5/MMA/EMA (55/12/24/9) | 22.3 | 18 | 102 | 0.31 |
| 10 BPM1/BPM6/MMA/BMA (60/10/24/6) | 23.0 | 17 | 107 | 0.32 |
| R5 BPM1/MMA (80/20) | 18.0 | 10 | 40 | 0.12 |

TABLE 3

| | Monomer Composition | Filler Kind | Filler Amount added | Light transmittance (%) | Bending strength (kgf/mm$^2$) | Flexural breaking strain (%) | Flexural breaking strain energy (kgf·mm) | Flexural breaking strain energy per volume (kgf·mm/mm$^3$) |
|---|---|---|---|---|---|---|---|---|
| 11 | BPM1/BPM5/MMA (55/15/30) | TiO$_2$ | 0.02 | 71 | 19.3 | 18 | 92 | 0.28 |
| 12 | BPM1/BPM5/MMA (55/15/30) | TiO$_2$ | 0.05 | 49 | 19.5 | 17 | 90 | 0.27 |
| R6 | BPM1/MMA (70/30) | SiO$_2$ | 9.0 | 72 | 18.2 | 8 | 19 | 0.06 |
| R7 | BPM1/BPM2/MMA (55/15/30) | SiO$_2$ | 20.0 | 52 | 11.0 | 3 | 7 | 0.02 |

Explanation of symbols

BPM1: compound of the formula (1) wherein m$_1$ and m$_2$ are 1 and R$_1$ is CH$_3$ BPM2: compound of the formula (1) wherein m$_1$ and m$_2$ are 2 and R$_1$ is CH$_3$ BPM3: compound of the formula (2) wherein n$_1$ and n$_2$ are 3 and R$_2$ is CH$_3$ BPM4: compound of the formula (2) wherein n$_1$ and n$_2$ are 4 and R$_2$ is CH$_3$ BPM5: compound of the formula (2) wherein n$_1$ and n$_2$ are 5 and R$_2$ is CH$_3$ BPM6: compound of the formula (2) wherein n$_1$ and n$_2$ are 6 and R$_2$ is CH$_3$ BPA5: compound of the formula (2) wherein n$_1$ and n$_2$ are 5 and R$_2$ is H BPA6: compound of the formula (2) wherein n$_1$ and n$_2$ are 6 and R$_2$ is H MMA: methyl methacrylate EMA: ethyl methacrylate CHM: 2,2'-bis(4-acryloxydiethoxycyclohexyl)propane BMA: n-butyl methacrylate As described above, the photosetting resin disclosed in the present invention has remarkably improved the defects of the conventional photosetting resins which are incapable of maintaining mechanical strength unless they are coated thinly on a substrate to form a coating film. The set or cured version of the present photosetting resin has satisfactorily high toughness by itself. Therefore, the photosetting resin of the present invention can be well applied to the production of resin molded articles.

Industrial Applicability

The photosetting resin of the present invention fully exhibits its advantageous characteristics when it is used for resin molded articles which are required to have strength and toughness. More specifically, the photosetting resin of this invention finds its particularly useful application to dental articles such as brackets for orthodontics, denture base, etc., and to precision machine parts such as miniature gears, pulleys, plastic screws, etc. It can be also used as a molding material for optical elements such as lens, prisms, etc.

What is claimed is:

1. A photosetting resin comprising a liquid monomer composition and a photopolymerization initiator, said resin when cured having a minimum value of flexural breaking strain energy per volume of at least 0.14 kg f mm/mm$^3$, said monomer composition containing a compound represented by the following formula (1) and a compound represented by the following formula (2) in a weight ratio within a range of from 90:10 to 66:34:

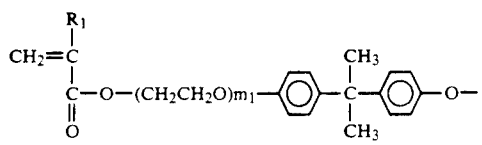

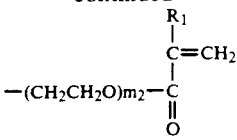

(wherein $R_1$ is H or $CH_3$, and $0 \leq m_1 + m_2 \leq 4$)

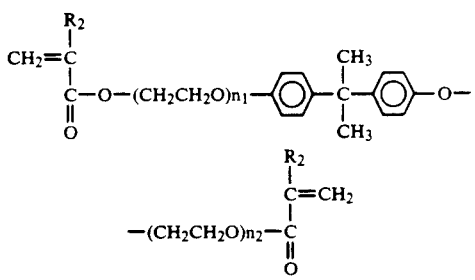

(wherein $R_2$ is H or $CH_3$, and $5 \leq n_1 + n_2 \leq 12$).

2. A photosetting resin according to claim 1 further containing a monofunctional (meth)acrylate in a weight ratio within a range of from 90:10 to 40:60 based on the liquid monomer composition.

3. A photosetting resin according to claim 1, containing 0.001 to 1% by weight of a filter selected from titanium dioxide, zirconium dioxide and alumina and having an average particle size of from 0.02 to 1 μm.

* * * * *